(12) United States Patent
Stevenson et al.

(10) Patent No.: US 10,362,982 B2
(45) Date of Patent: Jul. 30, 2019

(54) SPINAL IMPLANT SYSTEM AND METHOD

(71) Applicant: Warsaw Orthopedic, Inc., Warsaw, IN (US)

(72) Inventors: Tyler S. Stevenson, Tempe, AZ (US); Nicholas M. Benson, Cordova, TN (US); Newton H. Metcalf, Jr., Memphis, TN (US); Harold S. Taylor, Memphis, TN (US); Richard L. Brown, Mesa, AZ (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 15/582,055

(22) Filed: Apr. 28, 2017

(65) Prior Publication Data

US 2018/0310964 A1 Nov. 1, 2018

(51) Int. Cl.
| | |
|---|---|
| *A61B 17/70* | (2006.01) |
| *A61N 1/05* | (2006.01) |
| *A61N 1/32* | (2006.01) |
| *A61B 5/00* | (2006.01) |
| *A61N 1/378* | (2006.01) |
| *A61B 17/00* | (2006.01) |

(52) U.S. Cl.
CPC ........... *A61B 5/407* (2013.01); *A61B 5/6877* (2013.01); *A61B 17/7049* (2013.01); *A61N 1/0558* (2013.01); *A61N 1/326* (2013.01); *A61B 17/7032* (2013.01); *A61B 2017/00212* (2013.01); *A61N 1/3787* (2013.01)

(58) Field of Classification Search
CPC ............. A61B 17/7043; A61B 17/701; A61B 17/7032; A61B 5/407; A61B 5/6877; A61N 1/0558; A61N 1/326; A61N 1/3787
USPC .................................................. 606/246-279
See application file for complete search history.

(56) References Cited

U.S. PATENT DOCUMENTS

| | | | |
|---|---|---|---|
| 6,037,704 A | 3/2000 | Welle | |
| 6,083,226 A | 7/2000 | Fiz | |
| 6,113,600 A | 9/2000 | Drummond et al. | |
| 6,120,502 A | 9/2000 | Michelson | |
| 6,231,528 B1 | 5/2001 | Kaufman et al. | |
| 6,283,967 B1 | 9/2001 | Troxell et al. | |
| 6,322,527 B1 | 11/2001 | Talish | |
| 6,366,816 B1 | 4/2002 | Marchesi | |
| 6,432,108 B1 | 8/2002 | Burgess et al. | |
| 6,626,904 B1 | 9/2003 | Jammet et al. | |
| 6,652,473 B2 | 11/2003 | Kaufman et al. | |
| 6,678,562 B1 * | 1/2004 | Tepper ............... | A61B 17/6416 606/54 |
| 6,875,211 B2 | 4/2005 | Nichols et al. | |
| 8,078,283 B2 | 12/2011 | Cowan et al. | |

(Continued)

FOREIGN PATENT DOCUMENTS

| | | |
|---|---|---|
| DE | 4330680 A1 | 3/1995 |
| EP | 2916754 A4 | 7/2016 |

*Primary Examiner* — Pedro Philogene

(57) ABSTRACT

A spinal implant includes a link having a first surface and a second surface connectable with a spinal construct. The spinal construct is attachable with one or more vertebral levels. A plurality of electrodes includes at least one electrode disposed with the first surface and at least one electrode disposed with the second surface such that the electrodes conduct an electric current to stimulate tissue growth adjacent the spinal construct. Systems, surgical instruments and methods are disclosed.

20 Claims, 5 Drawing Sheets

(56) References Cited

U.S. PATENT DOCUMENTS

| | | | |
|---|---|---|---|
| 8,147,549 B2* | 4/2012 | Metcalf, Jr. | A61B 5/0031 623/17.11 |
| 8,197,515 B2 | 6/2012 | Levy et al. | |
| 8,380,319 B2* | 2/2013 | Berger | A61B 17/8605 607/37 |
| 8,494,644 B2 | 7/2013 | Cowan et al. | |
| 2006/0136004 A1 | 6/2006 | Cowan et al. | |
| 2006/0247635 A1* | 11/2006 | Gordon | A61B 17/7005 606/256 |
| 2006/0265074 A1 | 11/2006 | Krishna et al. | |
| 2007/0233090 A1* | 10/2007 | Naifeh | A61B 17/7023 606/258 |
| 2009/0177234 A1 | 7/2009 | Butler et al. | |
| 2009/0228046 A1 | 9/2009 | Garamszegi | |
| 2010/0049252 A1* | 2/2010 | Smisson, III | A61B 17/7043 606/250 |
| 2010/0094345 A1 | 4/2010 | Saidha et al. | |
| 2010/0106192 A1 | 4/2010 | Barry | |
| 2010/0274287 A1 | 10/2010 | Rouleau et al. | |
| 2011/0118852 A1 | 5/2011 | Evans | |
| 2012/0203278 A1 | 8/2012 | Gil et al. | |
| 2012/0271353 A1 | 10/2012 | Barry | |
| 2014/0114382 A1 | 4/2014 | Keun | |
| 2014/0257400 A1 | 9/2014 | Geroge et al. | |
| 2015/0182263 A1* | 7/2015 | Donner | A61B 17/7067 606/248 |
| 2016/0270927 A1* | 9/2016 | Zellmer | A61F 2/4455 |
| 2018/0126185 A1* | 5/2018 | Hochstenbach | A61N 2/02 |

\* cited by examiner

SPINAL IMPLANT SYSTEM AND METHOD

TECHNICAL FIELD

The present disclosure generally relates to medical devices for the treatment of musculoskeletal disorders, and more particularly to a surgical system and method for treating a spine.

BACKGROUND

Spinal pathologies and disorders such as degenerative disc disease, disc herniation, osteoporosis, spondylolisthesis, stenosis, tumor, scoliosis and other curvature abnormalities, kyphosis and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, partial or complete discectomy, corpectomy and laminectomy, and implantable prosthetics. As part of these surgical treatments, spinal constructs, such as, for example, bone fasteners, spinal rods and interbody devices can be used to provide stability to a treated region. For example, during surgical treatment, bone screws, rods and interbody implants can be delivered to a surgical site for fixation with bone to immobilize a joint. Such spinal constructs can be employed with bone growth promoting material to enhance fixation of the implants with the bone. This disclosure describes an improvement over these technologies.

SUMMARY

In one embodiment, a spinal implant is provided. The spinal implant includes a link having a first surface and a second surface connectable with a spinal construct. The spinal construct is attachable with one or more vertebral levels. A plurality of electrodes include at least one electrode disposed with the first surface and at least one electrode disposed with the second surface such that the electrodes conduct an electric current to stimulate tissue growth adjacent the spinal construct. In some embodiments, systems, spinal constructs, surgical instruments and methods are disclosed.

In one embodiment, a spinal construct is provided. The spinal construct includes a first spinal rod attached with a plurality of vertebral levels via a plurality of bone fasteners. A second spinal rod is attached with the plurality of vertebral levels via a plurality of bone fasteners. The spinal rods are disposed in a bi-lateral orientation with the vertebral levels. A transverse connector extends between a first end connected with the first spinal rod and a second end connected with the second spinal rod. The connector includes an anode and a cathode that are electrically isolated and oriented to conduct electric current in a bone growth stimulation path adjacent the rods and fasteners.

In one embodiment, a spinal implant system is provided. The spinal implant system includes a spinal construct attachable with one or more vertebral levels. A link is connected with the spinal construct and includes an anode and a cathode that are electrically isolated and oriented to conduct electric current in a bone growth stimulation path adjacent the spinal construct. An interbody implant is disposed with the one or more vertebral levels.

BRIEF DESCRIPTION OF THE DRAWINGS

The present disclosure will become more readily apparent from the specific description accompanied by the following drawings, in which.

DETAILED DESCRIPTION

Figure 1:
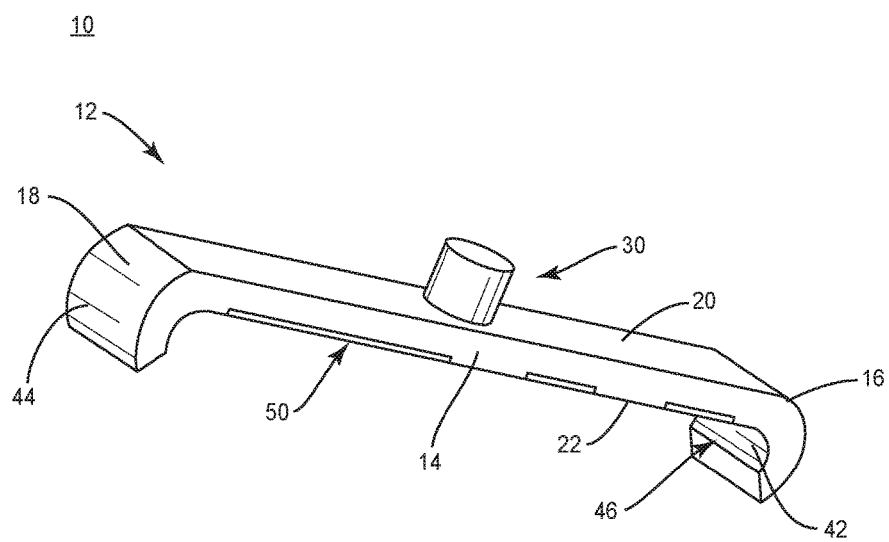
FIG. 1 is a perspective view of components of one embodiment of a surgical system in accordance with the principles of the present disclosure.

The exemplary embodiments of the surgical system and related methods of use disclosed are discussed in terms of medical devices for the treatment of musculoskeletal disorders and more particularly, in terms of a surgical system including a spinal implant and a method for treating a spine. In some embodiments, the surgical systems and methods of the present disclosure are employed with a spinal joint fusion, for example, with a cervical, thoracic, lumbar and/or sacral region of a spine.

In some embodiments, the present surgical system includes an implant, such as, for example, a bone stimulator. In some embodiments, the present surgical system comprises a spinal construct including a linking member with an integrated bone growth stimulator. In some embodiments, the present surgical system comprises a transverse link, stabilization spinal construct that provides a delivery device for electronic bone growth stimulation. In some embodiments, the spinal construct provides bi-lateral bone growth stimulation across a single or multiple fusion levels. In some embodiments, the present surgical system comprises an external power/communication source, such as, for example, a belt. In some embodiments, the present surgical system is employed with a method of aligning the external power/communication source by allowing the implant to be placed at a precise, fixed location that is both parallel to a patient's exterior and placed closer to the skin.

In some embodiments, the spinal construct can be implemented as a standalone device. In some embodiments, the spinal construct can be employed with a method of taking electronic sensor data and analyzing the progress of a fusion. In some embodiments, one or more components of the spinal construct can include sensors, for example, to monitor temperature, progress and/or activity. In some embodiments, the sensors may communicate with sensors embedded in an interbody implant. In some embodiments, the spinal construct comprises a power and communication hub to the interbody implant. In some embodiments, the spinal construct provides a bone growth stimulation path for therapy. In some embodiments, the spinal construct includes an anode placed on a cross link member, which would stimulate to a spinal rod and bone screws to selectively target bone growth.

In some embodiments, the spinal construct provides selective positioning of an anode to selectively orient a bone growth stimulation path. In some embodiments, the spinal construct includes a single anode that stimulates bilaterally for single or multiple fusion levels. In some embodiments, the spinal construct is employed with a method of therapy that can be induced directly to an interbody implant with the addition of a lead into the interbody implant. In some embodiments, the spinal construct provides power and captures sensor data from a cross link implant and/or an interbody implant. In some embodiments, the spinal construct comprises a hub to communicate with other implanted devices. In some embodiments, the spinal construct facilitates powering and communication with one or more components of the present surgical system with selective positioning and reducing distance to skin. In some embodiments, the spinal construct includes non-conducting material. In some embodiments, the spinal construct includes the non-conducting material that is disposed in a configuration to selectively deliver therapy directly to targeted areas. In some embodiments, the spinal construct delivers targeted therapy and captures quantified data relating to the progress of the fusion.

In some embodiments, the spinal construct includes a linking member having embedded electronics. In some embodiments, the spinal construct includes a positive anode fixed in space and spaced apart from an interbody implant disposed with a body. In some embodiments, the spinal construct includes a negative cathode that connects to one or more spinal rods to electrify the one or more spinal rods. In some embodiments, the spinal construct includes a cross link that provides a bone growth stimulation path from the anode to bone screws. In some embodiments, the spinal construct includes a cross link that provides a bi-lateral bone growth stimulation path across one or more spinal rods and one or more bone screws. In some embodiments, the spinal construct can be positioned with a body for communication with sensors embedded within an interbody cage disposed with the body. In some embodiments, the present surgical system includes a spinal construct and an external power coil. In some embodiments, the surgical system includes an implant, such as, for example, an interbody implant. In some embodiments, the interbody implant includes a bone growth stimulation interbody device. In some embodiments, the interbody implant includes an electronic bone growth stimulator enabled interbody cage. See, for example, the examples and disclosure of systems, implants and methods shown and described in U.S. patent application Ser. No. 14/792,256 filed by Stevenson et al. on Jul. 6, 2015, and published as U.S. Patent Application Publication No. 2017/0007420 on Jan. 12, 2017, the entire contents of which being incorporated by reference herein.

In some embodiments, the linking member includes a titanium coated surface on a superior surface and a titanium coated surface on an inferior surface. In some embodiments, the linking member includes anodes and cathodes to generate a selected electric field in and around the spinal construct to facilitate selective stimulation of bone growth around and through the spinal construct. In some embodiments, the anodes and cathodes can be embedded, snapped and/or coated with one or more surfaces of the linking member. In some embodiments, the linking member includes sidewall-embedded anode and cathode windows.

In some embodiments, the linking member includes electronic components that generate an electric current to stimulate bone growth. In some embodiments, the electronic components include diagnostics that provide diagnostic feedback and/or measure at least one diagnostic condition. In some embodiments, the diagnostics include, for example, embedded sensors for strain, stress and/or temperature. In some embodiments, the electronic components include remote power options using telemetry, such as, for example, near-field communication (NFC). In some embodiments, the electronic components include coils located outside a patient for powering the electronic components. In some embodiments, the electronic components include a NFC power harvesting integrated circuit. In some embodiments, the electronic components include an analog front end integrated circuit. In some embodiments, the electronic components include a microprocessor integrated circuit. In some embodiments, the electronic components include diagnostics that provide diagnostic feedback to guide and/or determine an optimum location for an external coil for powering the electronic components. In some embodiments, the electronic components include resonant circuits that provide an auto tuning feature to optimize communication between the electronic components and the remote power source, and/or other components of the surgical system. In some cases, various factors may contribute to detuning a resonant circuit, for example, implant depth, metal in the vicinity both inside and outside a body, and/or other factors. In some embodiments, the electronic components have an auto tuning feature and/or method that includes changing a tuning capacitor value and/or shifting operating frequency +/− over a range relative to a selected frequency. In some embodiments, the external coil and associated circuitry includes an auto tuning feature to optimize communication between the electronic components and the remote power source, and/or other components of the surgical system.

In some embodiments, the linking member includes electronic components that generate an electric field adjacent to and encompass a selected region of spinal tissue to stimulate bone growth. In some embodiments, the electronic components include one or more electrodes disposed in a configuration to generate an electric field over a selected region of spinal tissue to stimulate bone growth. In some embodiments, the electronic components include two electrodes configured to generate an electric field over a selected region of spinal tissue to stimulate bone growth. In some embodiments, the electronic components include one or more external devices, such as, for example, a tablet, computer and/or healthcare database that remotely communicate, such as, wireless technology, NFC technology and/or the transmission/reception of radio-frequency (RF) signals with the linking member. In some embodiments, the electronic components include micro-electronic systems, which may include micro-electronic substrates, a leadless stimulator placed in the linking member, and/or a hermetically sealed pressure sensor.

In some embodiments, the linking member includes an integration of electronic components into the linking member to monitor patient's recovery and may include an accelerometer, temperature sensor, strain gauge and/or a magnetometer. In some embodiments, the linking member provides electrical bone growth stimulation by implanting the linking member with a small circuit and an electrode; the circuit being powered from an external device via telemetry (NFC, for example). In some embodiments, the linking member comprises a bio-absorbable or partially bio-absorbable bone growth stimulator.

In some embodiments, the spinal construct includes a linking member with electronic components having variable power settings. In some embodiments, the spinal construct includes a linking member with electronic components that sense or detect impedance and/or collect impedance measurements as a proxy/indicator of fusion. In some embodiments, the spinal construct includes a linking member with electronic components that take diagnostic measurements from onboard sensors of one or more components of the spinal construct and/or an interbody cage. In some embodiments, the electronic components monitor diagnostic measurements of impedance or interpreting such impedance measurements as an indication of bone growth/fusion through/onto/around the spinal construct.

In some embodiments, the spinal construct includes a linking member having an electrical bone growth stimulator with increased fusion rates by applying an electrical stimulation across two electrodes in an area where fusion of a spine is desired. In some embodiments, the electrical stimulation creates an electric field which, in some embodiments, due to the piezo-resistive nature of bone tissue, causes a mechanical load across the bone. In some embodiments, the bone responds to the load with growth. In some embodiments, the linking member is molded over or otherwise encapsulates electronic components. In some embodiments, the linking member includes diagnostics that take an impedance measurement across the electrodes and use that measurement to determine if/how well bone has begun to grow or fused. In some embodiments, the linking member includes electronic components having an impedance measurement circuit to provide interrogable impedance measurements indicative of the growth of bone.

In some embodiments, the surgical system includes stages of treatment such that as bone growth begins, an increase in blood vessels at the interfaces occurs and bony tissue adjacent the spinal construct is generated. In some embodiments, these stages of treatment can include a detectable diagnostic that is detected with an impedance measurement. In some embodiments, this configuration allows a surgeon to request information from the linking member relating to the status of the fusion without needing medical imaging, such as, x-ray or magnetic resonance imaging (MRI). In some embodiments, the surgical system includes a linking member that stimulates bony tissue with an electric potential and causes bone to grow.

In some embodiments, the surgical system includes printed circuit board assembly inserts including up to two or three individual boards. In some embodiments, the individual boards are connected together in a desired shape before molding a PEEK mold over the electronic assembly. In some embodiments, the present system is configured to accommodate various implant sizes. In some embodiments, the surgical system includes a single electronic assembly that is connected by a flexible material, such as, for example, a flex circuit. In some embodiments, the flex circuit facilitates manufacture and the molding process of a linking member.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a" "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, muscle, ligaments, tendons, cartilage and/or bone unless specifically referred to otherwise.

Figure 2:
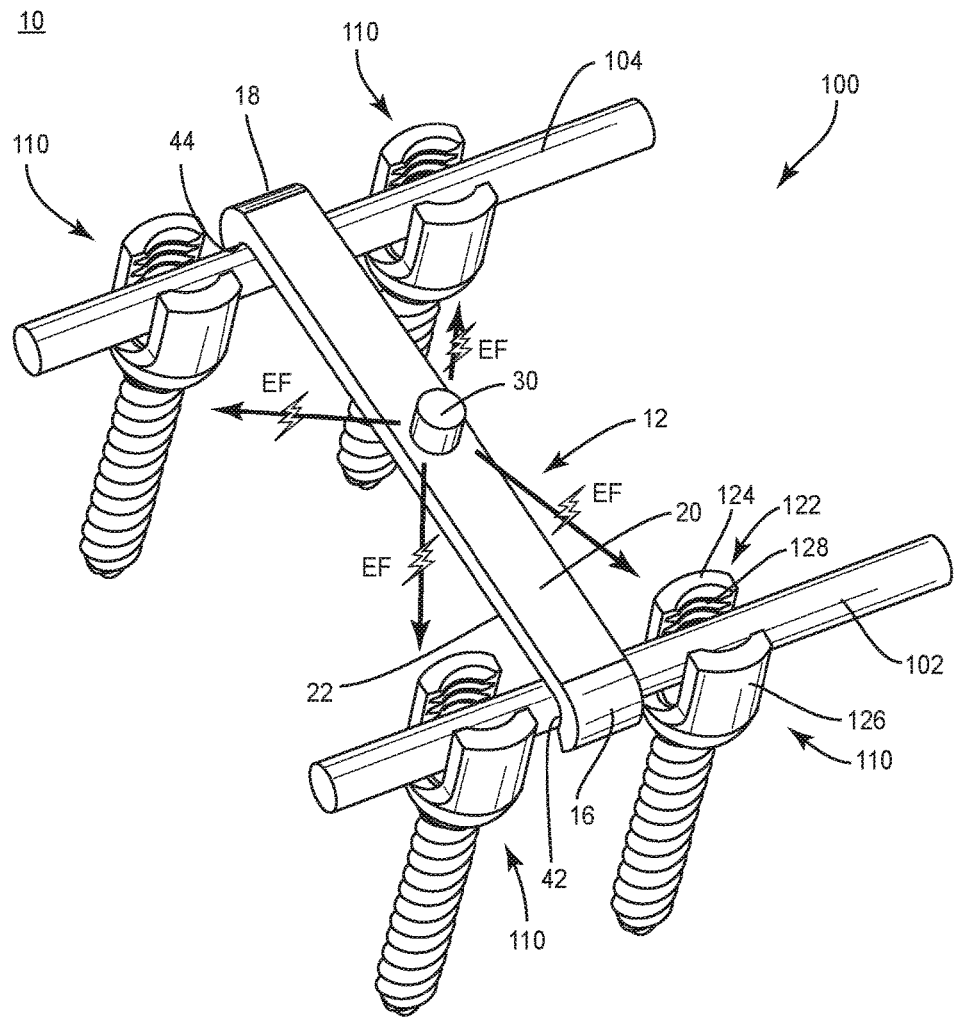
FIG. 2 is a perspective view of components of one embodiment of a surgical system in accordance with the principles of the present disclosure.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1 and 2, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites, unless specifically referred to otherwise. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, silver alloys, copper alloys, gold alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including PEEK, polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, fluorapatite, tri-calcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of spinal implant system 10 may have material composites, including the above materials, to achieve various desired characteristics such as conductivity, insulation and/or electrical isolation, strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein. In one embodiment, a spinal implant, as described herein, may be formed substantially of a biocompatible metal, such as titanium and selectively coated with a bone-growth promoting material, such as HA. In one embodiment, a spinal implant, as described herein, may be formed substantially of a biocompatible polymer, such as PEEK, and selectively coated with a biocompatible metal, such as titanium, or a bone-growth promoting material, such as HA. In some embodiments, titanium may be plasma sprayed onto surfaces of the spinal implant to modify a radiographic signature of the spinal implant and/or improve bony ongrowth to the spinal implant by application of a porous or semi-porous coating of titanium.

Spinal implant system 10 may be employed, for example, with minimally invasive procedures, including percutaneous techniques, mini-open surgical techniques and/or open surgical techniques to deliver and introduce one or more spinal implants at a surgical site within a subject body of a patient, which includes, for example, one or more vertebra. In some embodiments, the one or more spinal implants can include spinal constructs including one or more bone fasteners, spinal rods, interbody devices, connectors and/or plates. In some embodiments, spinal implant system 10 includes one or a plurality of selected implants for a particular surgical procedure. In some embodiments, spinal implant system 10 includes one or a plurality of implants selectively personalized to a patient.

Figure 3:
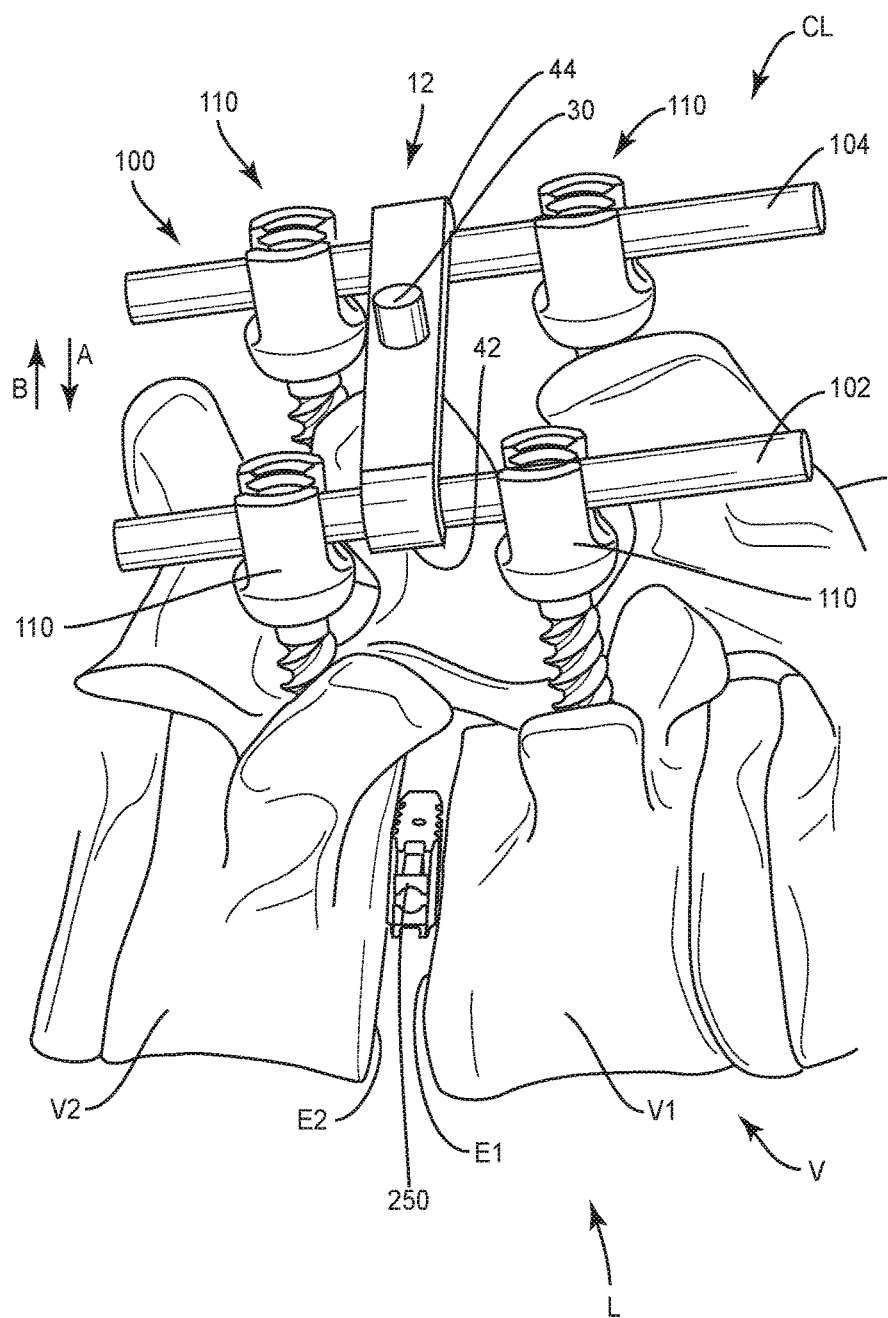
FIG. 3 is a perspective view of components of one embodiment of a surgical system in accordance with the principles of the present disclosure disposed with vertebrae.

Spinal implant system 10 comprises a spinal construct 100. Spinal construct 100 includes bone fasteners 110 attachable with one or a plurality of vertebral levels. Bone fasteners 110 are disposed with the vertebral levels along a lateral side and a contra-lateral side, as shown in FIG. 3. Spinal rods 102, 104 are attached with bone fasteners 110 in a bi-lateral orientation along the vertebral levels. A link, such as, for example, a connector 12 is engaged with spinal rods 102, 104 to conduct an electric current to stimulate tissue adjacent spinal construct 100.

Connector 12 is configured for transverse attachment with spinal rods 102, 104 of a spinal construct 100, as described herein. In some embodiments, connector 12 is configured for attachment with spinal rod 102 and/or spinal rod 104 in various orientations, such as, for example, perpendicular, parallel and/or other angular orientations such as acute or obtuse, and/or may be offset. Connector 12 includes a part 14 that extends between an end 16 and an end 18. In some embodiments, part 14 includes a substantially rectangular configuration. In some embodiments, part 14 may have various configurations, for example, round, oval, polygonal, irregular, tapered, offset, staggered, uniform and non-uniform.

Part 14 includes a surface 20 and a surface 22. In some embodiments, connector 12 is attached with spinal rods 102, 104 such that surface 22 is oriented to face an anterior direction, relative to a body B, as shown by arrow A in FIG. 3, and one or more vertebral levels of body B. In some embodiments, connector 12 is attached with spinal rods 102, 104 such that surface 20 is oriented to face a posterior direction, relative to a body B, as shown by arrow B in FIG. 3, and away from one or more vertebral levels of body B. In some embodiments, orientation of surface 20 in the posterior direction facilitates communication with a remote power source 200 (FIG. 4), as described herein.

Surface 20 includes an electrode 30 extending therefrom. Electrode 30 comprises an anode electrode of electronic components and/or circuitry of spinal implant system 10. Electrode 30 has a disc configuration. In some embodiments, electrode 30 may have alternate configurations, for example, round, oval, square, rectangular, polygonal, irregular, tapered, offset, staggered, uniform and non-uniform. Electrode 30 includes an electrically conductive material. In some embodiments, electrode 30 is fabricated from titanium. In some embodiments, the electrically conductive material of electrode 30 may be fabricated from various materials, such as, for example, metals described herein, electrolytes, superconductors, semi-conductors, plasmas and non-metallic conductors such as graphite and conductive polymers. In some embodiments, electrode 30 is disposed centrally along a length of surface 20. In some embodiments, electrode 30 is disposed at various positions along surface 20, such as, for example, offset or staggered. In some embodiments, electrode 30 comprises a cathode electrode.

Disposal of connector 12 with spinals rods 102, 104 positions anode electrode 30 relative to body B. In some embodiments, anode electrode 30 is positioned parallel to and adjacent skin of body B to optimize efficiency of bone growth stimulation. The orientation of anode electrode 30 with spinal construct 100 and/or vertebral tissue can be positioned to optimize a selected stimulation path and/or to conduct electric current through the vertebral tissue. In some embodiments, anode electrode 30 is positioned adjacent a posterior portion of vertebral tissue of body B to facilitate communication between anode electrode 30 and remote power source 200 by reducing a distance between anode electrode 30 and remote power source 200 through the skin of body B. In some embodiments, anode electrode 30 conducts electric current in a bilateral configuration along the vertebral tissue for a single level fusion or a multiple level fusion. In some embodiments, connector 12 comprises a communication hub and/or includes or is connected to associated electronics and circuitry to communicate with other implanted devices, as described herein.

Direct electric current is supplied to anode electrode 30, as described herein, such that anode electrode 30 conducts electric current through one or more components of spinal construct 100, vertebral tissue, an agent, interstitial tissue and/or fluids disposed adjacent spinal construct 100. Anode electrode 30 conducts the electric current through one or more components of spinal construct 100, for example, connector 12, bone fasteners 110 and/or rods 102, 104, to surface 22, as described herein, in a configuration to generate a selected electric field in, around, about, through and/or adjacent to connector 12 to selectively stimulate bone growth in vertebral tissue in, around, about, through and/or adjacent to spinal construct 100. In some embodiments, connector 12 is electrically coupled to one or more components of spinal construct 100. In some embodiments, connector 12 is electrically insulated from one or more components of spinal construct 100. In some embodiments, all or a portion of connector 12 is fabricated from a conductive material, such as, for example, titanium, which may be solid, porous, semi-porous and/or heterogeneous with another material. In some embodiments, anode electrode 30 may be removably attached to connector 12 or may be permanently affixed to connector 12.

Surface 22 includes an electrode, such as, for example, a cathode electrode of electronic components and/or circuitry of spinal implant system 10. Surface 22 extends between ends 16, 18. Surface 22 is spaced apart from anode electrode 30 to conduct direct electric current through one or more components of spinal construct 100, vertebral tissue, an agent, interstitial tissue and/or fluids disposed adjacent spinal construct 100, as described herein. End 16 is configured for engagement with spinal rod 102, as described herein. End 18 is configured for engagement with spinal rod 104, as described. End 16 includes an attachment mechanism, such as, for example, a hook 42 to facilitate a mating engagement with spinal rod 102. End 18 includes an attachment mechanism, such as, for example, a hook 44 to facilitate a mating engagement with spinal rod 104. In some embodiments, ends 16, 18 clamp and/or snap fit over rods 102, 104 such that surface 22 is in contact with a surface of rods 102, 104 to facilitate conduction with one or more components of spinal construct 100. In some embodiments, the attachment mechanism can include a clip, snap, key/keyslot, dovetail connector, lock, clamp, barb, penetrating member, flexible member, malleable member, tether and/or adhesive.

Surface 22 includes an electrically conductive material 46. In some embodiments, material 46 of surface 22 is fabricated from titanium. In some embodiments, electrically conductive material 46 of surface 22 may be fabricated from various materials, such as, for example, metals as described herein, electrolytes, superconductors, semi-conductors, plasmas and non-metallic conductors such as graphite and conductive polymers. In some embodiments, the cathode electrode may include one or more components of spinal construct 100, for example, rods 102, 104 and/or bone fasteners 110. In some embodiments, the cathode electrode may include one or more components of spinal construct 100 that are selectively configured and/or disposed to resist and/or prevent bone growth adjacent selected locations and/or components of spinal implant system 10, and/or selected portions of vertebral tissue. In some embodiments, one or more components of the cathode electrode may include a nonconductive material, such as, for example, silicone or epoxy to resist and/or prevent bone growth adjacent selected locations and/or components of spinal implant system 10, and/or selected portions of vertebral tissue.

Surface 22 conducts direct electric current through one or more components of spinal construct 100, vertebral tissue, an agent, interstitial tissue and/or fluids disposed adjacent spinal construct 100. Surface 22 conducts the electric current through connector 12 and/or bone fasteners 110 and rods 102, 104, from anode electrode 30, as described herein, to generate a selected electric field EF, as shown in FIG. 2, in, around, about, through and/or adjacent to spinal construct 100 to selectively stimulate bone growth in vertebral tissue in, around, about, through and/or adjacent interbody spinal construct 100. Electrode 30 comprises an anode electrode and surface 22 comprises a cathode electrode, which are selectively oriented with connector 12 to generate an electric field EF, as shown in FIG. 2, in, around, about, through and/or adjacent to spinal construct 100 to selectively stimulate bone growth in, around, about, through and/or adjacent spinal construct 100 at one or multiple vertebral levels.

In some embodiments, the electrodes of connector 12 are selectively arranged to generate a selected electric field in, around, about, through and/or adjacent to connector 12 to selectively stimulate tissue growth in vertebral tissue, as described herein. In some embodiments, anode electrode 30 is disposed remote from bone growth locations. In some embodiments, connector 12 includes a plurality of anode electrodes and a plurality of cathode electrodes that are selectively configured with connector 12 to generate a selectively configured electric field in, around, about, through and/or adjacent to spinal construct 100 to selectively stimulate bone growth in vertebral tissue, as described herein. In some embodiments, connector 12 is molded, during a manufacturing and/or fabrication method for producing connector 12, with electronic components, as described herein. In some embodiments, connector 12 is molded with a printed circuit board assembly and electrodes, as described herein. In some embodiments, connector 12 includes electronic components disposed in a selected configuration and PEEK material is molded with, on or about the electronic components to form connector 12 and/or to encapsulate the electronic components with connector 12.

Connector 12 includes electronic components, such as, for example, a printed circuit board assembly 50, which includes one or more components for delivering electric current to the electrodes, powering connector 12 and/or detecting/sensing diagnostics, and is suitable for implantation. Circuit board assembly 50 includes a non-conductive component, such as, for example, a substrate. The substrate is connected with conductive circuitry and/or coils configured to conduct a current to anode electrode 30 and/or surface 22 to generate electric field EF adjacent connector 12 to selectively stimulate tissue growth adjacent spinal construct 100. In some embodiments, circuit board assembly 50 is a flexible printed circuit. In some embodiments, the substrate includes conductive pads and other features etched from conductive metal sheets and laminated onto the substrate. In some embodiments, one or more components of connector 12 may include a non-ferrous material to minimize interference with remote powering and/or communication of data with connector 12. In some embodiments, the non-ferrous material includes titanium grade 2.

The substrate is connected with and/or includes circuitry and one or more integrated circuits or micro-electronic chips for delivering electric current to the electrodes, powering connector 12 and/or detecting/sensing diagnostics. In some embodiments, the one or more integrated circuits disposed with circuit board assembly 50 can remotely communicate with electronic components of spinal implant system 10 disposed outside or external to a body of a patient. In some embodiments, circuit board assembly 50 can remotely communicate with such external electronic components to power connector 12 and/or transfer, transmit and/or receive data relating to connector 12 including treatment and/or diagnostics, as described herein. In some embodiments, the remote communication can include a wireless link, such as, for example, Bluetooth, NFC, WiFi, MICS, and/or the remote communication systems and methods as described in U.S. Pat. No. 5,683,432 "Adaptive Performance-Optimizing Communication System for Communicating with an Implantable Medical Device" to Goedeke, et al., the contents of which being hereby incorporated by reference in its entirety.

Figure 4:
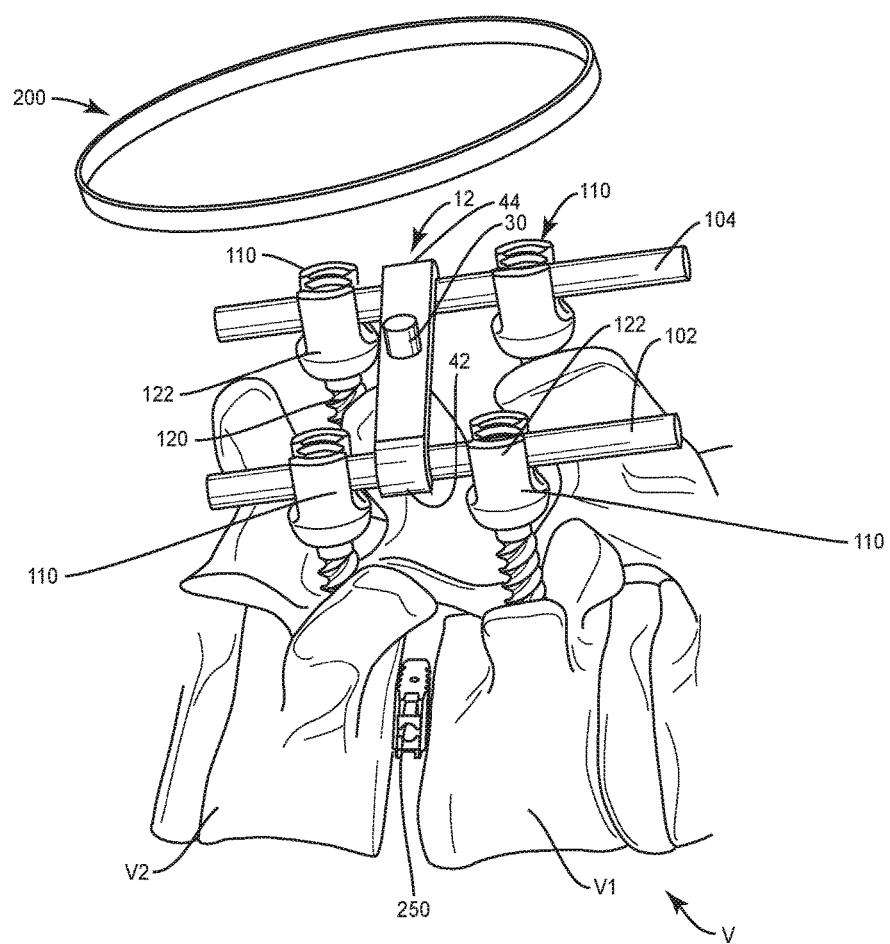
FIG. 4 is a perspective view of components of one embodiment of a surgical system in accordance with the principles of the present disclosure disposed with vertebrae.

For example, in some embodiments, spinal implant system 10 includes a remote power source 200, as shown in FIG. 4. In some embodiments, power source 200 includes a belt worn about body B to dispose power source 200 outside or external to body B and circuit board assembly 50. Power source 200 includes a NFC integrated circuit device for powering connector 12 and conducting electric current through anode electrode 30 and surface 22. The NFC device is configured for inductive communication with remote power source 200 for power harvesting of a communication signal for powering connector 12. The NFC device may comprise various commercially available integrated circuit devices, see, for example, but not limited to, the RF430 microcontroller distributed by Texas Instruments RF430. In some embodiments, remote power source 200 includes a computer, cell phone, PDA, laptop, surgical instrument, clothing, accessory such as a bag, wallet, pocketbook, backpack or other device mounted with body B, which includes electronic components for communicating with the NFC device, as described herein. In some embodiments, the NFC device operates and/or communicates with remote power source 200 within a radio frequency band of 13.56 MHz, with a bandwidth of approximately 2 MHz.

The NFC device employs magnetic induction with, for example, a reader, such as, for example, disposed with connector 12 and power source 200. The NFC device includes a power harvesting integrated circuit that enables connector 12 to establish radio communication at a short distance to supply power to charge circuit board assembly 50. The substrate includes a magnetic receiving antenna, such as, for example, a plurality of antenna disposed in series. In some embodiments, the antenna includes coils and/or solenoids. The antenna is connected with the NFC device to convert nearby magnetic fields into energy such that anode electrode 30 and surface 22 conduct electric current to selectively stimulate tissue growth adjacent spinal construct 100, as described herein.

Power source 200 emits a small electric current to create a magnetic field that bridges the physical space between power source 200 and connector 12 implanted within body B. The NFC device is electrically connected with electronic components of circuit board assembly 50 to charge circuit board assembly 50 disposed with connector 12 by power source 200 disposed external relative to body B. Power source 200 radiates energy through a cutaneous barrier, such as, for example, the skin of body B to adjacent connector 12. An electromagnetic field is generated by a transmitting coil within power source 200 to transmit power across the skin to the plurality of antenna disposed with connector 12. The plurality of antenna transfers the received power to connector 12 for charging/powering. In some embodiments, the NFC device is disposed adjacent a dorsal location of a body.

In some embodiments, the NFC device remotely communicates with a device, such as, for example, a computer that is disposed outside or external to body B to transfer, transmit and/or receive data relating to connector 12 including treatment and/or diagnostic information obtained from connector 12. Connector 12 includes diagnostic sensor electronics connected with one or more sensors disposed about spinal construct 100, anode electrode 30 and/or surface 22 and an analog integrated circuit device connected with diagnostic sensor electronics and the NFC device to obtain and store data received from connector 12 and surrounding tissue. The diagnostic sensor electronics may comprise various commercially available integrated circuit devices, see, for example, but not limited to, the AD5933 Impedance Converter Network Analyzer distributed by Analog Devices. The integrated circuit device may comprise various commercially available integrated circuit devices, see, for example, but not limited to, the RF430 microcontroller distributed by Texas Instruments RF430.

In some embodiments, the diagnostic sensor electronics and/or the analog device gather information, such as, for example, loading information, pressure information, tension information, motion information, alignment or misalignment information and/or temperature, relating to one or more components of spinal construct 100, vertebral tissue or bone growth disposed adjacent spinal construct 100 and/or treatment, as described herein. The computer remotely communicates with the NFC device, as described herein, to collect data from connector 12 via the diagnostic sensor electronics. In some embodiments, a reader is disposed on body B that communicates with the computer. In some embodiments, power source 200, as described herein, includes the reader. The reader emits a small electric current that creates a magnetic field to bridge the physical space between the reader and interbody implant 250. The electric field is received by the NFC device and converted into electrical impulses to communicate data and diagnostics, relating to connector 12 and/or treatment to the computer, as described herein.

The diagnostic sensor electronics provides feedback and/or measures one or more diagnostic conditions. In some embodiments, the diagnostics include, for example, embedded sensors for strain, stress and/or temperature. The diagnostic sensor electronics sense and transmit to the computer various diagnostic indicia, and in some embodiments, diagnose and respond to such measurements, such as, for example, in the context of a spinal implant surgery. In some embodiments, a surgeon can monitor a patient after surgery, and make adjustments to one or more components of spinal construct 100 including connector 12 and/or treatment to avoid a subsequent surgery. In some embodiments, this configuration allows one or more components of spinal construct 100 including connector 12 and/or treatment to be corrected or modified based on changes that take place subsequent to surgery, and/or for selected and remote changes to diagnostic conditions inside body B. In some embodiments, the diagnostic sensor electronics indicate fusion rate of spinal construct 100 with vertebrae. In some embodiments, the diagnostic sensor electronics provide diagnostic feedback to guide and/or determine an optimum location for an external coil for powering the electronic components. In some embodiments, the diagnostic sensor electronics include resonant circuits that provide an auto tuning feature to optimize communication between the electronic components of connector 12 and power source 200. In some embodiments, the auto tuning feature includes changing a tuning capacitor value and/or shifting operating frequency +/− over a range relative to a selected frequency.

In some embodiments, the diagnostic sensor electronics sense or detect impedance and/or collect impedance measurements as a proxy/indicator of fusion based on configuration of tissue. In some embodiments, the diagnostic sensor electronics monitor diagnostic measurements of impedance or interpreting such impedance measurements as an indication of bone growth/fusion in, around, about, through and/or adjacent to spinal construct 100. For example, in some embodiments, the diagnostic sensor electronics sense or detect impedance and/or collect impedance measurements based on the configuration of tissue such as fat, muscle, bone and blood.

In some embodiments, the components of spinal implant system 10 can be selected for a particular surgical procedure and/or from alternate components of a spinal implant kit based on one or more criteria. In some embodiments, the one or more criteria include, for example, anatomical parameters, implant parameters and/or surgical procedure parameters, as described herein. In some embodiments, the anatomical parameters can include condition, quality, configuration and/or dimension of selected anatomy, for example, one or more disc space dimensions, disc height, disc tissue, and/or one or more vertebra dimensions, vertebra/vertebrae height and/or vertebral tissue, and/or a footprint associated with vertebral tissue including vertebrae and intervertebral discs. In some embodiments, the footprint can include the area defined by vertebral tissue, such as, for example, an endplate surface of one or more vertebra.

Bone fasteners 110 include a shaft 120 and an implant receiver 122 configured for disposal of spinal rods 102, 104. In some embodiments, spinal implant system 10 includes one or more bone fasteners comprising multi-axial screws, uni-axial screws, fixed axis screws, sagittal adjusting screws, transverse sagittal adjusting screws, pedicle screws, uni-planar screws, facet screws, tissue penetrating screws, conventional screws, expanding screws and/or posts. In some embodiments, one or more components of spinal construct 100, for example, spinal rods 102, 104, bone fasteners 110 and/or interbody implant 250, may include diagnostic sensor electronics, similar to the diagnostic sensor electronics of connector 12 described herein. In some embodiments, the diagnostic sensor electronics of connector 12 communicate, similar to that described herein, with the diagnostic sensor electronics of the one or more components of spinal construct 100, for example, spinal rods 102, 104, bone fasteners 110 and/or interbody implant 250.

Figure 5:
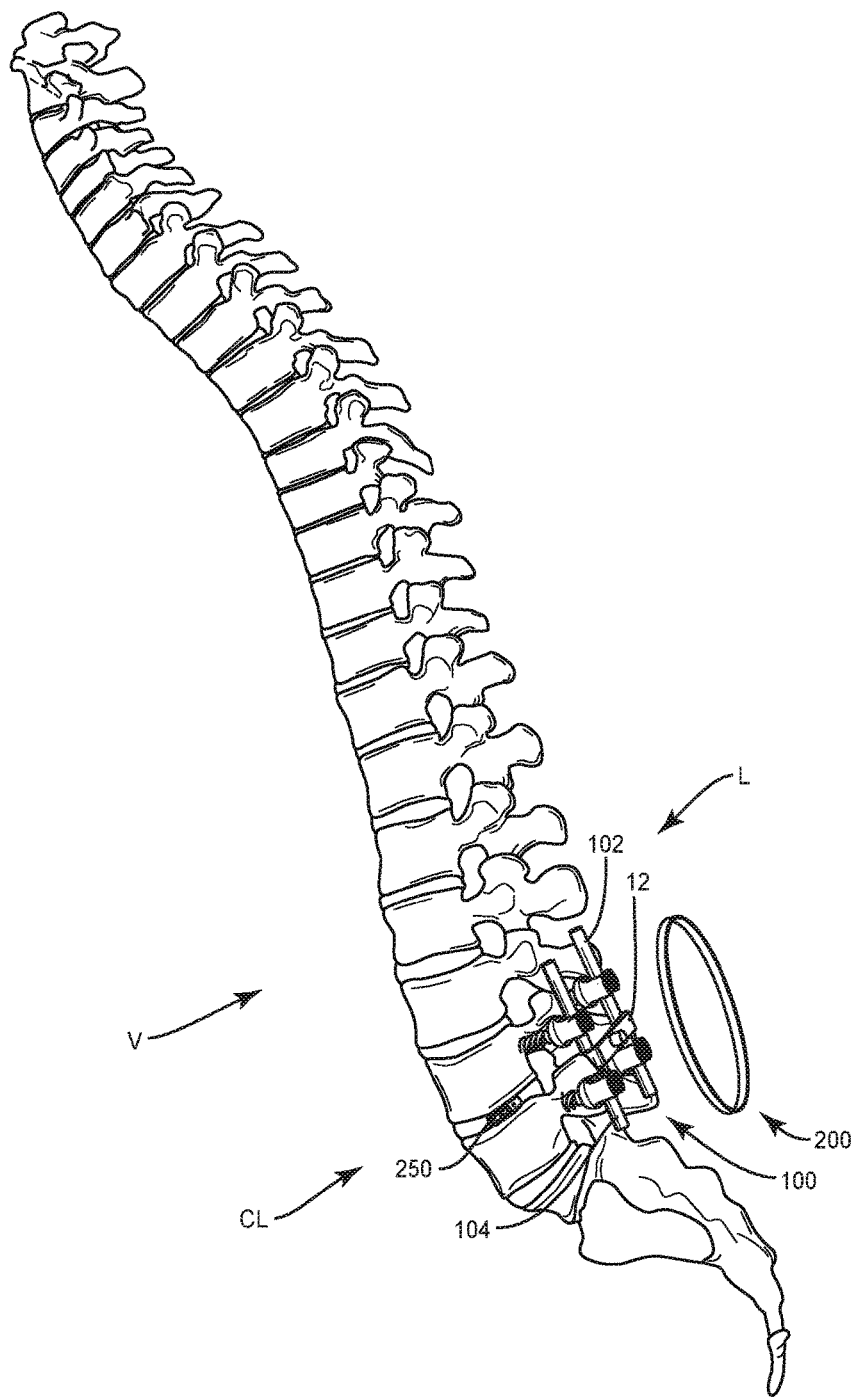
FIG. 5 is a perspective view of components of one embodiment of a surgical system in accordance with the principles of the present disclosure disposed with vertebrae.

In assembly, operation and use, as shown in FIGS. 3-5, spinal implant system 10, similar to the systems and methods described herein, is disposed with tissue, such as, for example, vertebrae V of patient body B for treatment of a spinal disorder, such as those described herein, affecting a section of a spine of a patient. In some embodiments, the surgical procedure parameters can include one or a plurality of vertebra, uni-lateral treatment, bi-lateral treatment, PLIF, TLIF, DLIF, ACDF, OLIF and/or ALIF. In some embodiments, the components of interbody implant 12 can be selected prior to surgery. For example, a surgeon can conduct imaging diagnosis and/or pre-operative planning using medical imaging, as described herein, to measure anatomical parameters employed to determine implant parameters.

An incision is made in the body of a patient and a cutting instrument (not shown) creates a surgical pathway for implantation of components of spinal implant system 10 adjacent a surgical site including vertebrae V. A preparation instrument (not shown) can be employed to prepare tissue surfaces of vertebrae V, as well as for aspiration and irrigation of a surgical region.

The components of spinal construct 100 are delivered to the surgical site for disposal with vertebrae V in connection with the surgical treatment. Pilot holes or the like are made in vertebrae V1 and V2 for receiving bone fasteners 110. A driver (not shown) is disposed adjacent vertebrae V at a surgical site and is manipulated to drive, torque, insert or otherwise connect bone fasteners 110 with vertebrae V1 and V2. Bone fasteners 110 are engaged with vertebrae V in a bilateral orientation along a lateral side L and a contra-lateral side CL of vertebrae V. Spinal rod 102 is contoured and disposed within receivers 122 on lateral side L and spinal rod 104 is disposed within receivers 122 on contra-lateral side CL.

Connector 12 is attached with spinal rods 102, 104 such that hooks 42, 44 are positioned onto rods 102, 104 to facilitate conduction with surface 22. Surface 22 is oriented to face an anterior direction, relative to a body B, as shown by arrow A in FIG. 3, and vertebrae V, and surface 20 is oriented to face a posterior direction, relative to a body B, as shown by arrow B in FIG. 3, and away from vertebrae V. Connector 12 is oriented with spinals rods 102, 104 to position anode electrode 30 parallel and adjacent the skin of body B in a configuration to optimize a selected stimulation path including electric field EF (FIG. 2), for example, bilaterally from anode electrode 30 to bone fasteners 110. Anode electrode 30 is positioned adjacent a posterior portion of vertebrae V to communicate with remote power source 200, as described herein. Power source 200 is attached with body B, as described herein.

Connector 12 is powered with remote power source 200, as described herein, for applying electrical stimulation to vertebrae V for bone growth to facilitate fusion. Surface 22 conducts direct electric current through one or more components of spinal construct 100, vertebral tissue, an agent, interstitial tissue and/or fluids disposed adjacent spinal construct 100, from anode electrode 30, as described herein, to generate a selected electric field EF (FIG. 2) in the tissue of vertebrae V. Electric field EF provides a bilateral stimulation path across spinal rods 102, 104 and bone fasteners 110 to selectively stimulate bone growth in tissue in, around, about, through and/or adjacent spinal construct 100. This configuration causes a mechanical load across the bone, tissue, agents, interstitial tissue and/or fluids adjacent spinal construct 100 and the bone and tissue responds to the load with bone growth to facilitate fusion of spinal construct 100 with tissue of vertebrae V. In some embodiments, diagnostic sensor electronics provide feedback and/or measure diagnostic conditions of vertebrae V, as described herein.

In some embodiments, an inserter (not shown) is connected with an interbody implant 250. The inserter delivers interbody implant 250 through the incision to the surgical site for implantation into an intervertebral space between endplate surfaces E1, E2 such that interbody implant 250 is disposed with vertebrae V1, V2 for treatment of a spinal disorder. In some embodiments, interbody implant 250 is visualized by fluoroscopy and oriented before malleting into the intervertebral space.

In some embodiments, interbody implant 250 includes an electronic bone growth stimulator enabled interbody cage. See, for example, the examples and disclosure of an electronic bone growth stimulator enabled interbody cage shown and described in U.S. Patent Application Publication No. 2017/0007420, the entire contents of which being incorporated by reference herein. For example, connector 12 comprises a communication and powering hub that communicates with interbody implant 250. Connector 12 includes or is connected to sensors, as described herein, which communicate with diagnostic sensors embedded within interbody implant 250. The sensors disposed with interbody implant 250 provide feedback and/or measure diagnostic conditions of vertebrae V, similar to that described herein with regard to connector 12. In some embodiments, connector 12 provides a remote power source and/or employs remote power source 200, similar to anode electrode 30 described herein, for powering interbody implant 250 to apply electrical stimulation to bone, tissue, agents, interstitial tissue and/or fluids adjacent endplates E1, E2 and interbody implant 250 for bone growth to facilitate fusion, similar to that described herein.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiopaque markers may be included for identification under x-ray, fluoroscopy, CT, MRI or other imaging techniques. In some embodiments, the use of surgical navigation, microsurgical and image guided technologies may be employed to access, view and repair spinal deterioration or damage, with the aid of spinal implant system 10. In some embodiments, spinal implant system 10 may include one or a plurality of plates, connectors and/or bone fasteners for use with a single vertebral level or a plurality of vertebral levels.

In one embodiment, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant system comprising:
    a link including a first surface and a second surface connectable with a spinal construct, the spinal construct being attachable with one or more vertebral levels, the link extending between a first end and an opposite second end, the second end being integrally formed with the first end, the first end and the second end each comprising an attachment mechanism configured to matingly engage the spinal construct;
    a plurality of electrodes including at least one electrode disposed with the first surface and at least one electrode disposed with the second surface, the electrodes being configured to conduct an electric current to stimulate tissue growth adjacent the spinal construct; and
    a spinal implant,
    wherein the link is configured to act as a power hub to the spinal implant to allow the spinal implant to apply electrical stimulation.

2. A spinal implant system as recited in claim 1, wherein the first surface includes an anode and the second surface includes a cathode, the anode being electrically isolated from the cathode and disposed to conduct an electric current to stimulate tissue growth adjacent the spinal construct.

3. A spinal implant system as recited in claim 1, wherein the link includes a transverse connector connecting the first end with the second end.

4. A spinal implant system as recited in claim 1, wherein each attachment mechanism comprises a hook.

5. A spinal implant system as recited in claim 1, wherein the attachment mechanism of the first end includes a first hook engageable with a first spinal rod of the spinal construct and the attachment mechanism of the second end includes a second hook engageable with a second spinal rod of the spinal construct.

6. A spinal implant system as recited in claim 1, wherein the link includes a transverse connector connecting the first end with the second end, the at least one electrode of the first surface being centrally disposed with the connector.

7. A spinal implant system as recited in claim 1, wherein the link includes at least one diagnostic sensor in communication with at least one diagnostic sensor of the spinal implant to measure diagnostic conditions of the one or more vertebral levels.

8. A spinal implant system as recited in claim 1, wherein the at least one electrode of the second surface is oriented to face the one or more vertebral levels.

9. A spinal implant system as recited in claim 1, wherein the at least one electrode of the second surface is disposed with the ends.

10. A spinal implant system as recited in claim 1, wherein the electrodes are disposed in a selected configuration relative to the spinal construct to conduct the electric current through the spinal construct including at least one bone fastener.

11. A spinal implant system as recited in claim 1, wherein the link includes an integrated circuit for wireless communication with an external power source.

12. A spinal implant system as recited in claim 1, wherein the link includes an integrated circuit for wireless communication with the spinal construct.

13. A spinal implant system as recited in claim 1, wherein the link includes at least one diagnostic sensor configured to communicate with at least one diagnostic sensor disposed with the spinal construct.

14. A spinal implant system comprising:
    a spinal construct comprising:
        a first spinal rod configured to be attached with a plurality of vertebral levels via a plurality of bone fasteners, and
        a second spinal rod configured to be attached with the plurality of vertebral levels via a plurality of bone fasteners, the spinal rods being configured for disposal in a bi-lateral orientation with the vertebral levels, and
        a transverse connector extending between a first end connected with the first spinal rod and a second end connected with the second spinal rod, the second end being integrally formed with the first end, the connector including an anode and a cathode, the anode and the cathode being electrically isolated and oriented to conduct an electric current through the rods and fasteners to stimulate tissue growth; and a spinal implant, wherein the connector is configured to act as a power hub to the spinal implant to allow the spinal implant to apply electrical stimulation.

15. A spinal implant system as recited in claim 14, wherein the first end includes an attachment mechanism including a portion of the cathode engageable with the first spinal rod and the second end includes an attachment mechanism including a portion of the cathode engageable with the second spinal rod.

16. A spinal implant system as recited in claim 14, wherein the connector includes an integrated circuit for wireless communication with an external power source.

17. A spinal implant system comprising:

a spinal construct attachable with one or more vertebral levels;

a link connected with the spinal construct and including an anode and a cathode, the electrode and the cathode being electrically isolated and oriented to conduct electric current in a bone growth stimulation path adjacent the spinal construct, the link extending between a first end and an opposite second end, the second end being integrally formed with the first end, the first end and the second end each comprising an attachment mechanism configured to matingly engage the spinal construct; and an interbody implant configured to be disposed with the one or more vertebral levels, the interbody implant comprising a sensor configured to communicate with the link, wherein the link is configured to act as a power hub to the interbody implant to allow the interbody implant to apply electrical stimulation.

18. A spinal implant system as recited in claim 17, wherein the link includes an integrated circuit for wireless communication with an external power source.

19. A spinal implant system as recited in claim 17, wherein the link includes an integrated circuit for wireless communication with the spinal construct.

20. A spinal implant system as recited in claim 17, wherein the link communicates with the interbody implant.

* * * * *